(12) United States Patent
Martin et al.

(10) Patent No.: US 8,702,714 B2
(45) Date of Patent: Apr. 22, 2014

(54) INSTRUMENTS FOR TOTAL KNEE ARTHROPLASTY

(75) Inventors: Jeffrey W. Martin, St. Louis, MO (US); Kevin Wong, Cordova, TN (US); Brian R. Harris, Jr., Cordova, TN (US)

(73) Assignee: Microsoft Orthopedics Holdings Inc., Tiel (NL)

( * ) Notice: Subject to any disclaimer, the term of this patent is extended or adjusted under 35 U.S.C. 154(b) by 1733 days.

(21) Appl. No.: 11/684,395

(22) Filed: Mar. 9, 2007

(65) Prior Publication Data

US 2007/0213738 A1 Sep. 13, 2007

Related U.S. Application Data

(60) Provisional application No. 60/780,635, filed on Mar. 9, 2006.

(51) Int. Cl.
*A61F 5/00* (2006.01)
*A61B 17/56* (2006.01)
*A61B 17/58* (2006.01)

(52) U.S. Cl.
USPC ............................... 606/88; 606/87

(58) Field of Classification Search
USPC ......... 606/86 R, 87–89, 96–98; 403/384, 398
See application file for complete search history.

(56) References Cited

U.S. PATENT DOCUMENTS

| 3,757,705 | A | * | 9/1973 | Maslow | 108/147.13 |
|---|---|---|---|---|---|
| 4,474,177 | A | * | 10/1984 | Whiteside | 606/80 |
| 4,952,213 | A | * | 8/1990 | Bowman et al. | 606/79 |
| 5,002,545 | A | * | 3/1991 | Whiteside et al. | 606/80 |
| 5,047,032 | A | * | 9/1991 | Jellicoe | 606/83 |
| 5,342,367 | A | * | 8/1994 | Ferrante et al. | 606/86 R |
| 5,417,694 | A | * | 5/1995 | Marik et al. | 606/88 |
| 5,474,559 | A | * | 12/1995 | Bertin et al. | 606/89 |
| 5,611,802 | A | * | 3/1997 | Samuelson et al. | 606/86 R |
| 5,649,928 | A | * | 7/1997 | Grundei | 606/88 |
| 5,662,656 | A | * | 9/1997 | White | 606/88 |
| 5,683,397 | A | * | 11/1997 | Vendrely et al. | 606/88 |

* cited by examiner

*Primary Examiner* — Christian Sevilla
(74) *Attorney, Agent, or Firm* — Duane Morris LLP

(57) ABSTRACT

An instrument assembly for resecting a distal femur for receipt of a knee implant, comprising an intramedullary rod and resection instruments. A valgus portion of the intramedullary rod has series of engagement members positioned to provide a plurality of engagement positions for use in fixing the resection instruments on the valgus portion. The resection instruments are configured to selectively engage and selectively lock on the valgus rod at the engagement positions via the engagement members. The engagement members preferably comprise pairs of substantially vertical indents arranged in parallel along opposing sides of said valgus portions. The resection instruments preferably engages and locks to said engagement members via a sliding rod engagement member. The resection instruments preferably include a distal cut guide having a distal resection slot and a femoral resection block.

16 Claims, 6 Drawing Sheets

INSTRUMENTS FOR TOTAL KNEE ARTHROPLASTY

CROSS REFERENCE TO RELATED APPLICATIONS

This application claims priority to and incorporates by reference U.S. Provisional Patent Application 60/780,635, filed Mar. 9, 2006, which is pending.

STATEMENT REGARDING FEDERALLY SPONSORED RESEARCH

Not applicable

FIELD OF THE INVENTION

The present invention relates to knee surgery, and more particularly to femoral resection instruments and methods that are particularly suited for minimally invasive total knee arthroplasty surgical procedures.

BACKGROUND OF THE INVENTION

Total knee implants have been around for many years. Over the years, various instruments have been developed for preparing the distal femur and the proximal tibia for receipt of knee implants. Performance of a knee replacement surgery typically includes modification of one, or both, of the proximal end of the tibia and the distal end of the femur to have a shape that accommodates the tibial and femoral components, respectively, of the knee prosthesis. Modification typically involves some type of cutting procedure, e.g., with a bone saw, to prepare planar surfaces on the femur for attachment of the femoral component. An effective attachment of the femoral component to the femur is facilitated by cutting the femur at appropriate depths and angles that match the dimensions and angles of the attachment (i.e., non-articulating) surfaces on the underside of the femoral component. The femur, due to its complex geometry (e.g., lateral and medial condyles and intracondylar notch) can be particularly difficult to shape and therefore benefits greatly from accurate cuts. In addition, proper sizing of the components is important to ensure that the knee prosthesis has adequate stability and range of motion. To this end, various calipers and resection guides have been developed that measure the tibia and femur to determine appropriate sizes for the femoral and tibial components. Examples of instruments and methods are found in applicant's U.S. Pat. No. 4,474,117, U.S. Patent Application Publication No. 2005/0209600A1, and U.S. Patent Publication No. 2006/0241634A1, which are incorporated herein by reference.

Despite the effectiveness of knee replacement systems, additional improvements in systems and methods for preparing the distal femur for attachment of a femoral component are always desirable.

OBJECTS AND BRIEF SUMMARY OF THE INVENTION

It is an object of the invention to provide improved instruments for femoral knee resections that eliminate the use of a stylus or pins. These and other objects of the invention are achieved by providing an instrument assembly for use in preparing a distal femur for receipt of an implant, the instrument assembly comprising an intramedullary rod and associated resection instruments. The intramedullary rod has an intramedullary portion and a valgus portion. The valgus portion has a series of engagement members thereon positioned to provide a plurality of engagement positions for use in fixing resection instruments on the valgus portion at the engagement positions. The resection instruments are configured to selectively engage and selectively lock on the valgus rod at the engagement positions via the engagement members. The engagement members of the valgus rod preferably comprise pairs of substantially vertical indents arranged in parallel along opposing sides of said valgus portions. The resection instrument preferably engages and locks to the engagement members via a rod engagement member. The rod engagement member is slidingly disposed in the resection instrument and has a pair of opposing rail members. A retaining means is preferably provided for retaining the rod engagement member in the resection instrument. Each rail member has a detent on an internal side thereof. The detents are sized and configured to selectively slide into and engage the pairs of indents to thereby lock the resection instrument in a selected engagement position. Detents of the rail members are preferably arranged to slide along opposing medial and lateral edges of a valgus rod aperture portion of the resection instrument. The valgus rod aperture portion is preferably configured to closely receive the valgus rod in at least a generally medial-lateral orientation.

The resection instruments preferably include a distal cut guide having a distal resection slot and a femoral resection block configured for making resections corresponding to an internal box geometry of a femoral implant. In a preferred embodiment, a main body of the distal cut guide is provided with a pair of drill guides. Each drill guide has a drill aperture therethrough, the drill apertures positioned to coincide with femoral pegs on the femoral resection block for use in a establishing a position for the femoral resection block on the femur.

The distal cut guide is preferably configured for anterior-posterior adjustment of the distal cut guide relative to the valgus rod. In a preferred embodiment, the anterior-posterior adjustment is provided by a valgus rod mount slidingly engaged to a main body portion of the distal cut guide, the valgus rod mount having a valgus rod aperture sized and configured to closely receive the valgus rod, so as to substantially prevent rotation of the valgus rod mount relative to the valgus rod. A selective locking mechanism is preferably provided for use in selectively locking the valgus rod mount on the distal cut guide such that the main body portion can no longer translate relative to the valgus rod.

The valgus rod preferably has a narrow medial-lateral width to facilitate resection of the femur while the intramedullary rod is in an intramedullary canal of the femur. Opposing medial and lateral sides of the valgus rod are preferably substantially flat and lengthwise.

In addition to the foregoing, other features discussed below form part of the invention.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in the figures, the invention generally comprises a set of pinless resection instruments for preparing the distal femur for receipt of a femoral implant, along with methods of using the instruments.

Figure 1A:
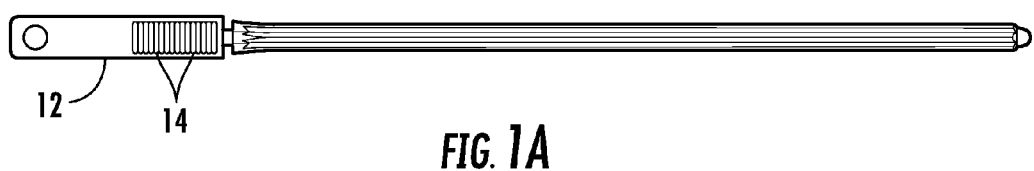
FIGS. 1A-B provide views of one preferred embodiment of a femoral intramedullary rod configured for use in the invention.
Figure 1B:
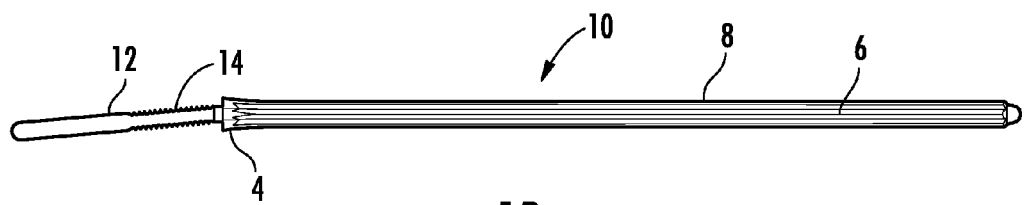

The pinless procedure is carried out with the use of a specially configured intramedullary rod 10 ("IM rod"). As shown in FIGS. 1A and 1B, the valgus rod 12 portion of the IM rod 10 has a narrow medial-lateral configuration. The narrow medial-lateral profile of the valgus rod 12 facilitates resection of the femur while the IM rod 10 is in the femur of the patient. A series of opposing grooves 14 are formed along the medial and lateral sides of the valgus rod 12. The grooves 14 serve as locking positions for a distal cut guide 20 and a femoral resection block 70, as will be described in further detail below. The medial and lateral sides of the valgus rod 12 are preferably flat, which provides additional engagement surface between the grooves 14 and a rod engagement member of the distal cut guide 20 and the femoral resection block 70.

The intramedullary stem portion 8 of the IM rod 10 is preferably provided with a plurality of lengthwise straight cutting flutes or splines 6 to prevent rotation of the IM rod 10 in the IM canal. A distal or training end of the stem 8 preferably has a tapered shoulder 4 formed thereon. The tapered shoulder 4 allows for a press fit fixation between the shoulder 4 and the IM canal, which further serves to maintain the IM rod 10 in a fixed, non-rotational relationship with the IM canal. The tapered shoulder 4 eliminates the use of fins on the stem portion 8. As indicated in FIG. 1B, the valgus rod 12 is preferably set at a valgus angle (i.e., the axis of the valgus rod 12 is offset from the axis of the IM rod 10) in order to match the femoral resections to the mechanical axis of the patient's femur, in a manner known to those skilled in the art and described in U.S. Pat. No. 4,474,177, which is incorporated herein by reference. The valgus rod 12 will typically have a valgus angle of about 3 to about 7 degrees. An instrument set will typically include a set of rods 10 having various valgus angles, e.g. 3, 5 and 7 degrees, so that the surgeon can select the appropriate valgus angle for the particular patient. During use, the surgeon lines up the valgus rod 12 with the trochlear groove of the femur.

Figure 4:
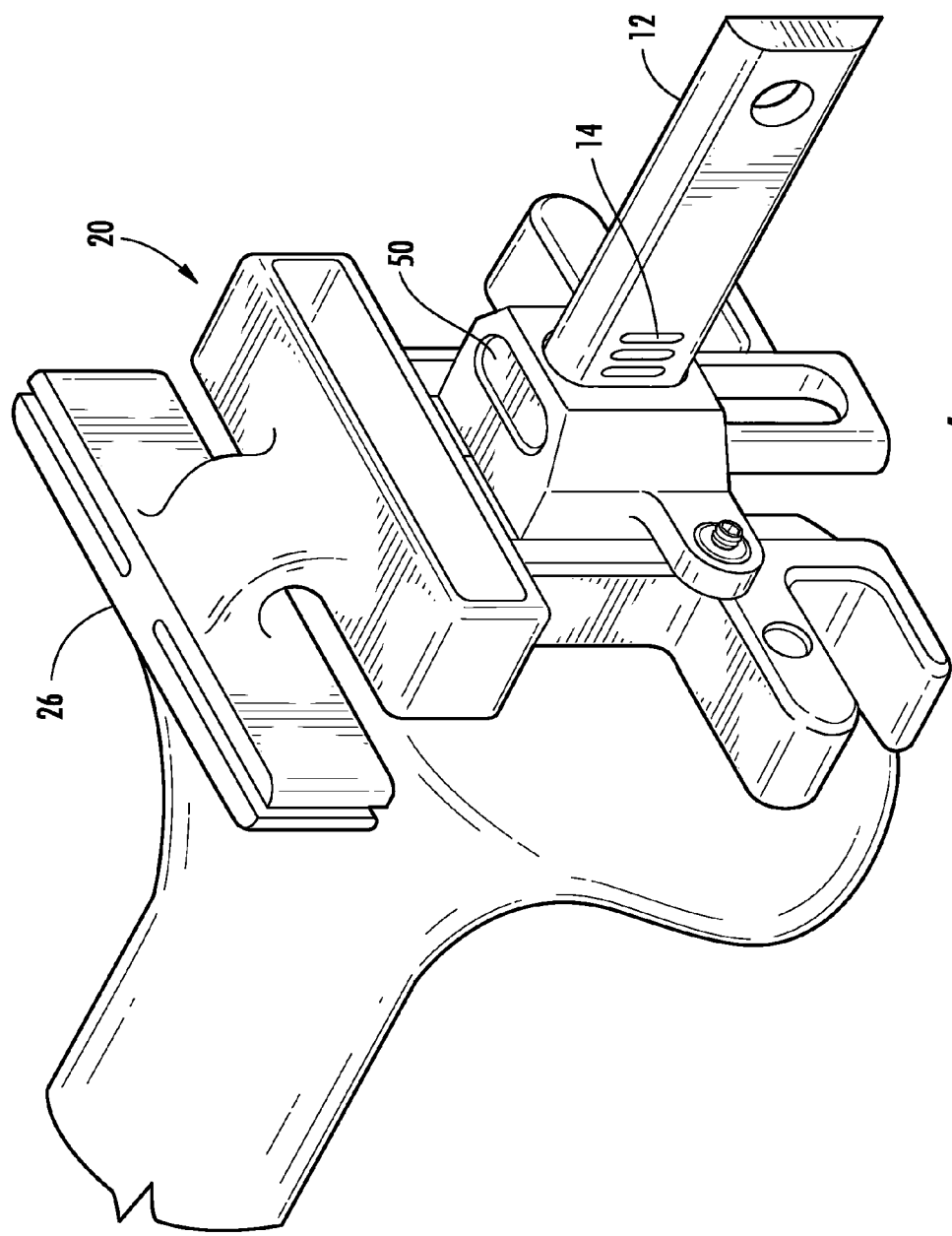
FIG. 4 shows one preferred embodiment of a distal cut guide mounted on an intramedullary rod according to the invention.

FIG. 2 provides views of a distal cut guide 20 for use in a pinless TKA procedure. As shown in FIG. 4, the distal cut guide 20 is configured to mount on the valgus rod 12 portion of the IM rod 10. The distal cut guide 20 includes a main body portion 22, which generally supports and interconnects the other components of the distal cut guide 20. The distal cut guide 20 is preferably provided with a stylus guide 24 having a stylus slot 25 passing therethrough. The stylus slot 25 can take various forms, but preferably has a lengthwise configuration to allow for visualization along the anterior surface of the femur, as shown in FIG. 2B. The bottom or posterior edge of the stylus slot 25 is preferably positioned to align with the anterior edge of the femoral resection block 70, in order to assist the surgeon in visualizing the placement of the femoral resection block 70.

As shown in FIG. 2, the distal cut guide 20 includes a distal resection guide 26 having a resection slot 27. The distal resection guide 26 is configured for use in making a distal resection while the IM rod 10 is in the femur of the patient. As shown particularly in FIG. 2D, the distal resection guide 26 is preferably provided with a pair of resection slots 27, with each slot 27 opening along one of the opposing sides of the distal resection guide. Opposing walls of the distal resection guide 26 are joined by a central portion 29. The central portion 29 is positioned to align with the valgus rod 12 when the distal cut guide 20 is mounted on the valgus rod 12. The distal resection guide 26 may be attached to the stylus guide 24 or main body portion 22 via a distal resection guide support member 28.

The main body 22 of the distal cut guide 20 is provided with a pair of drill guides 30. Each drill guide 30 has a drill aperture 31 therethrough. The drill apertures 31 are positioned to coincide with femoral pegs 39 on the femoral resection block 70.

Figure 2A:
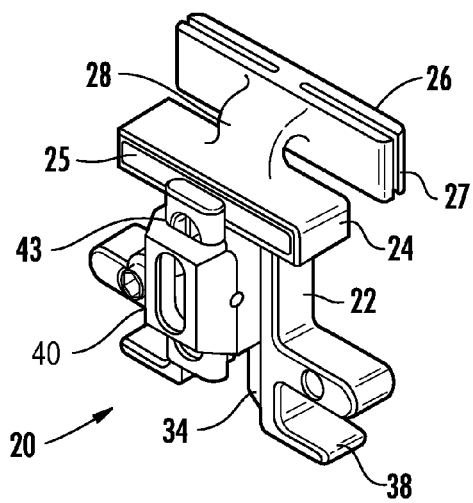
FIGS. 2A-2E provide views of one preferred embodiment of a distal cut guide and components thereof for use in the invention.
Figure 2B:
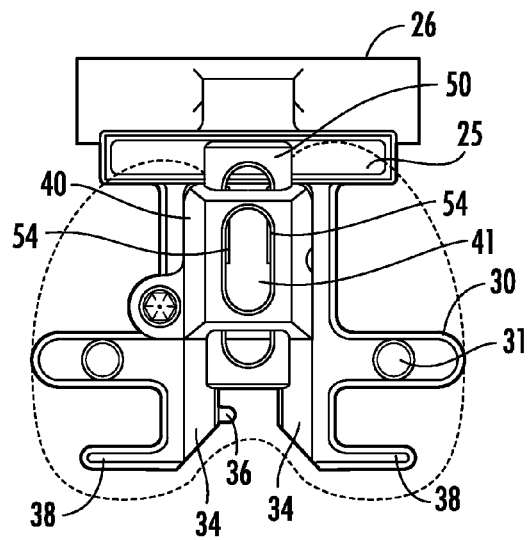
Figure 2C:
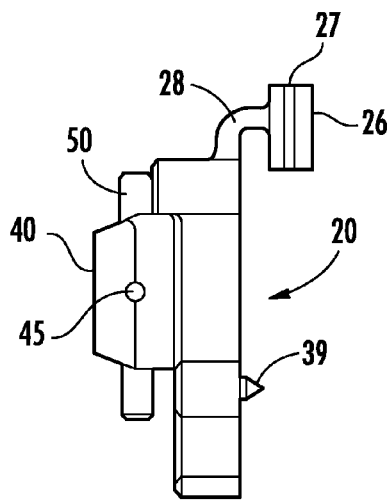
Figure 2D:
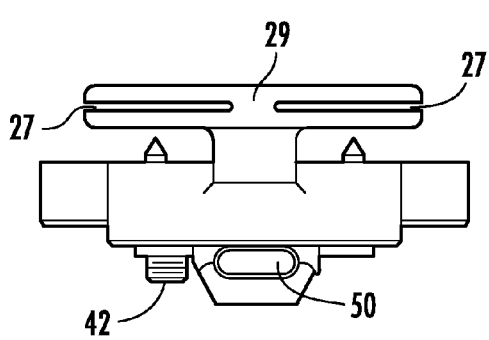

The main body portion 22 of the distal cut guide 20 is configured for sliding engagement with an IM rod mount 40. In one preferred embodiment, the main body portion 22 is configured to have two downwardly depending legs, with opposing rail members 34 positioned along an interior side of each leg. As indicated in FIG. 2, the IM rod mount 40 is configured to slide along the rail members 34 in the anterior-posterior orientation. As shown in FIG. 2B, to prevent the IM rod mount 40 from separating from the posterior end of the rail members 34, a stop member 36, such as a set pin, can be positioned adjacent a posterior end of one or both rail members 34. In the embodiment of FIG. 2, a lower surface of the stylus guide 24 prevents the IM rod mount 40 from disengaging anteriorly from the rail members 34.

To assist the surgeon in visualizing the location of the posterior resection, a pair of posterior arms 38 can be provided on the main body portion 22. The posterior arms 38 are preferably positioned and configured such that a flat posterior edge of each posterior arm 38 coincides with the anterior or upper edge of the posterior resection slot 75P of the femoral resection block 70.

A pair of femoral pegs 39 can be provided on the proximal or leading face of the distal cut guide 20. The femoral pegs 39 have a sharp, pointed configuration, which allows the pegs 39 to readily engage the distal surface of the uncut femur to assist in stabilizing the distal cut guide 20 on the valgus rod 12. The femoral pegs 39 are sized such that they do not interfere with the distal cut.

As noted above, the IM rod mount 40 is slidingly engaged to the main body portion 22, such that the main body portion 22 can be adjusted anteriorly-posteriorly relative to the valgus rod 12. The IM rod mount 40 includes an IM rod aperture 41. The IM rod aperture 41 is sized and configured to closely receive the valgus portion 12 of the IM rod 10, so as to substantially prevent rotation or substantial movement of the IM rod mount 40 relative to the valgus rod 12. A selective locking mechanism, such as set screw 42, is positioned for use in selectively fixing or locking the position of the IM rod mount 40 on the distal cut guide 20. With the IM rod mount 40 locked to the main body portion 22, the main body portion 22 can no longer translate relative to the valgus rod 12.

Figure 2E:
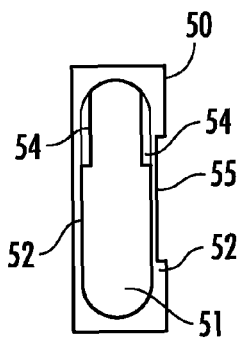

The IM rod mount 40 is configured to receive an IM rod engagement member 50. The IM rod engagement member 50 is slidably engaged to IM rod mount 40, such as via the engagement track or cavity 43 indicated in FIG. 2A. Details of a preferred embodiment of an IM rod engagement member 50 are shown in FIG. 2E. The IM rod engagement member 50 includes an IM rod aperture 51 generally formed by a pair of opposing rail members 52. The IM rod aperture 51 is longer than the A-P dimension of the valgus rod 12, such that the IM rod engagement member 50 can translate anteriorly-posteriorly along the valgus rod 12.

The IM rod engagement member 50 includes a stop means for selectively engaging the grooves 14 of the valgus rod 12. In the embodiment of FIG. 2E, the stop means is a pair of lengthwise IM rod detents 54 formed along anterior inner surfaces of the rail members 52. Each IM rod detent 54 is configured to selectively engage a selected one of the grooves 14 of the valgus rod 12. In the embodiment shown in FIG. 2, the distal cut guide 20 is selectively locked onto the valgus rod 12 by pushing or dropping the IM rod engagement member 50 down (posteriorly) until the IM rod detents 54 engage a selected pair of the opposing grooves 14. Note that the anterior portion of IM rod aperture 51 is configured to rest on the anterior surface of the valgus rod 12. If the surgeon is not satisfied with the position of the distal cut guide 20, the surgeon can disengage the distal cut guide 20 from the valgus rod 12 by pulling up on the IM rod engagement member 50 until the IM rod detents 54 disengage from the valgus rod 12.

A retaining means 55 is provided for use in retaining the IM rod engagement member 50 in the IM rod mount 40. In the configuration shown in FIG. 2E, the retaining means 55 is a cutout 55 portion having opposing shoulders for engaging a retaining member 45 of the IM rod mount 40.

The configuration of the distal cut guide 20 shown in FIG. 2 allows a surgeon to size the femur, set rotation, set A-P positioning, make a distal resection, and drill peg holes with a single instrument. In most anatomical conditions, only one of the condyles (typically the medical condyle) will contact the proximal face of the distal cut guide 20. The contact between the distal cut guide 20 and the condyle is used to stabilize the distal cut guide 20. When making the distal cut, the surgeon preferably starts by cutting the distal condyle that is not touching the distal cut guide 20. If the surgeon makes the initial cut on the condyle that is touching the distal cut guide 20, this will leave a space between the cut condyle and the distal cut 20, which will tend to destabilize the distal cut guide 20.

Once the distal cut guide 20 has been used to make the distal cut and resection block holes have been drilled in the distal femur, the IM rod engagement member 50 is disengaged from the valgus rod 12 and the distal cut guide 20 is removed from the rod 12. A femoral resection block 70 is then used to make the box cuts of the distal femur. In a preferred embodiment, the instruments are provided in the form of a surgical kit, with the kit including a pair of distal cut guides 20 and matching femoral resection blocks 70 for each size of femoral implant (e.g. six sets of guides 20 and blocks 70 corresponding to implant sizes 1-6). The kit also preferably includes a set of femoral implants of various sizes (e.g. sizes 1-6), with the implants configured for implantation on the resections made by respectively sized resection blocks 70.

FIG. 3 provides views of a preferred embodiment of a femoral resection block 70. The femoral resection block 70 has an IM rod aperture 71 for use in mounting the femoral resection block 70 on the valgus rod 12. The femoral resection block 70 is provided with a means of locking or fixing the resection block 70 in a selected position on the valgus rod 12. In one preferred embodiment shown in FIG. 3, selective engagement is provided by an IM rod engagement member 90 that is disposed in a sliding relation to the resection block 70. The IM engagement member 90 slides into an engagement track 77 formed in the resection block 70. Details of one preferred embodiment of an IM rod engagement member 90 are shown in FIG. 3D. The engagement member 90 is provided with opposing rail members 92, which form an IM rod slot 91. The rail members 92 are held in a fixed relation to one another via an anterior cross bar 96, a lower surface of which is configured to rest along tan anterior surface of the resection block 70. A tab 98 preferably extends from the cross bar 96 for use by the surgeon in manipulating the IM rod engagement member 90 to engage or disengage the valgus rod 12.

IM rod detents 94 are provided along inner surfaces of the rail members 92. Like the detents 54 of the distal resection guide 20, each IM rod detent 94 is configured to selectively engage a selected one of the grooves 14 of the valgus rod 12. In the embodiment shown in FIG. 3, the resection guide 70 is selectively locked onto the valgus rod 12 by pushing or dropping the IM rod engagement member 90 down (posteriorly) until the IM rod detents 94 engage a selected pair of the opposing grooves 14.

Figure 3A:
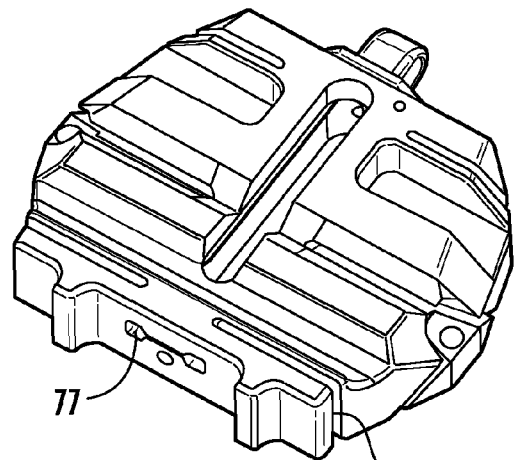
FIGS. 3A-3D provide views of one preferred embodiment of a femoral resection block for use in the invention.
Figure 3B:
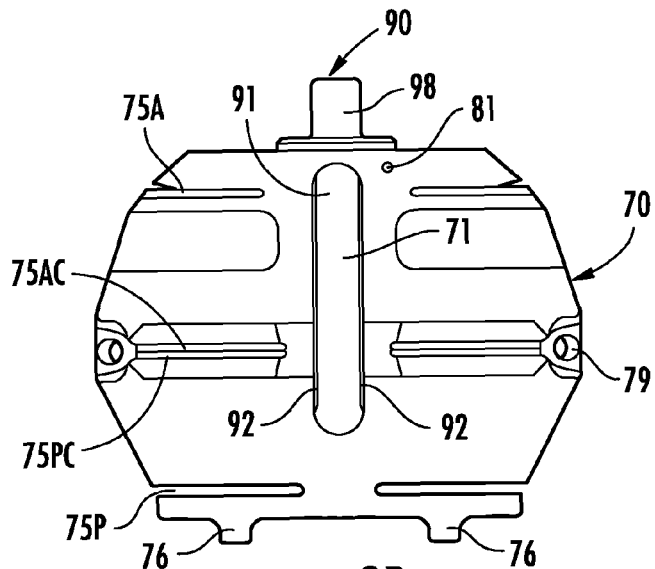
Figure 3C:
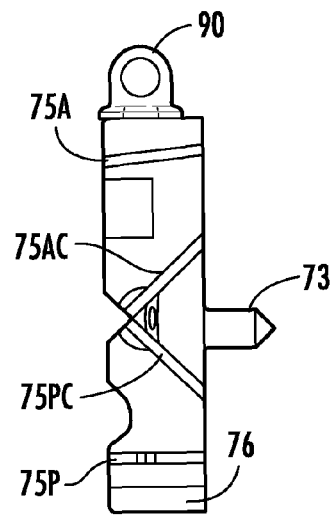
Figure 3D:
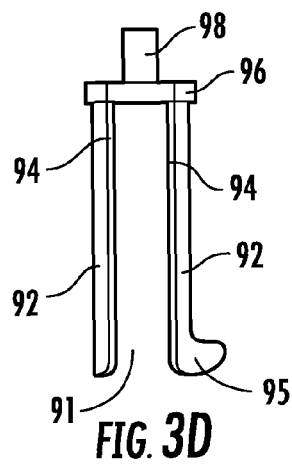

To prevent the IM rod engagement member 90 from inadvertently separating from the resection block 70, the IM rod engagement member 90 can be provided with a retaining means 95, such as the retaining foot 95 formed on a lower end of a rail member 92, as shown in FIG. 3D. A retaining means 81, such as a set screw or plugs 81, can be provided on the body of the resection block 70 for use in retaining the IM rod engagement member 90 in the resection block 70.

Femoral pegs 73 are provided on a posterior or leading surface of the resection block 70. The femoral pegs 73 are sized and positioned to coincide with the drill apertures 31 of the drill guides 30, such that the pegs 73 can be inserted in holes drilled into the distal cut femur via the drill apertures 31. These features assure accurate transfer of reference points between the distal cut guide 20 and the femoral resection block 70.

The femoral resection block has an anterior resection slot 75A, a posterior resection slot 75P, an anterior chamfer resection block 75AC, and a posterior chamfer reselection slot 75PC. All of the resections slots are preferably broken into two slots, so as to facilitate resectioning around the valgus rod 12. All of the reselection slots preferably open along respective lateral edges of the block 70.

One or more posterior positioning members 76 preferably extend from a posterior edge of the femoral resection block 70. The posterior positioning members 76 are sized to match the posterior edge of the femoral implant, in order to assist the surgeon in visualizing final positioning of the implant.

Although the engagement portion of the instruments has been described as having a negative engagement (i.e. grooves 14) on the valgus rod 12 and a positive engagement member (e.g. detent 54) on the corresponding IM rod engagement member 50, 90, it will be appreciated that the engagements could be reversed without departing from the spirit and scope of the invention. In other words, a positive engagement, such as a series of detents, could be provided on the valgus rod 12 and a negative engagement, such as grooves, could be provided on the rod engagement member 50, 90.

Although the instruments are designed for use without pins, situations may arise in which the surgeon will find it advantageous to pin the femoral resection block 70 to the femur, such as when the quality of the cancellous bone is poor. For this purpose, pin holes 79 are preferably provided on the femoral resection block 70. As shown in FIG. 3B, the pin holes 79 are preferably located on the medial and lateral sides of the resection block 70, such that the pin holes 79 are positioned over cortical bone.

The components of the kit are preferably arranged in a convenient format, such as in a surgical tray or case. However, the kit components do not have to be packaged or delivered together, provided that they are assembled or collected together in the operating room for use at the time of surgery.

A preferred method of use of the instruments will now be described. The size of the femur is preferably approximated through pre-operative x-ray templating. The pinless instruments of the invention are designed to allow for femoral sizing without the use of stylus. Sizing is performed by visually aligning the top and bottom of the distal resection guide 20 with the anterior cortex and posterior condyles, respectively. To assist in better visualizing the anterior cortex, a rongeur is preferably used early in the procedure to create a small notch 100 at the deepest point of the anterior trochlear groove. The base of the notch should be flush with the anterior cortex. The surgeon drills an opening in the femoral canal for insertion of the IM rod 10, in a manner known to those of skill in the art. The hole is either placed medial and anterior to the anteromedial corner of the intercondylar notch, or in the center of the trochlear groove.

Figure 5:
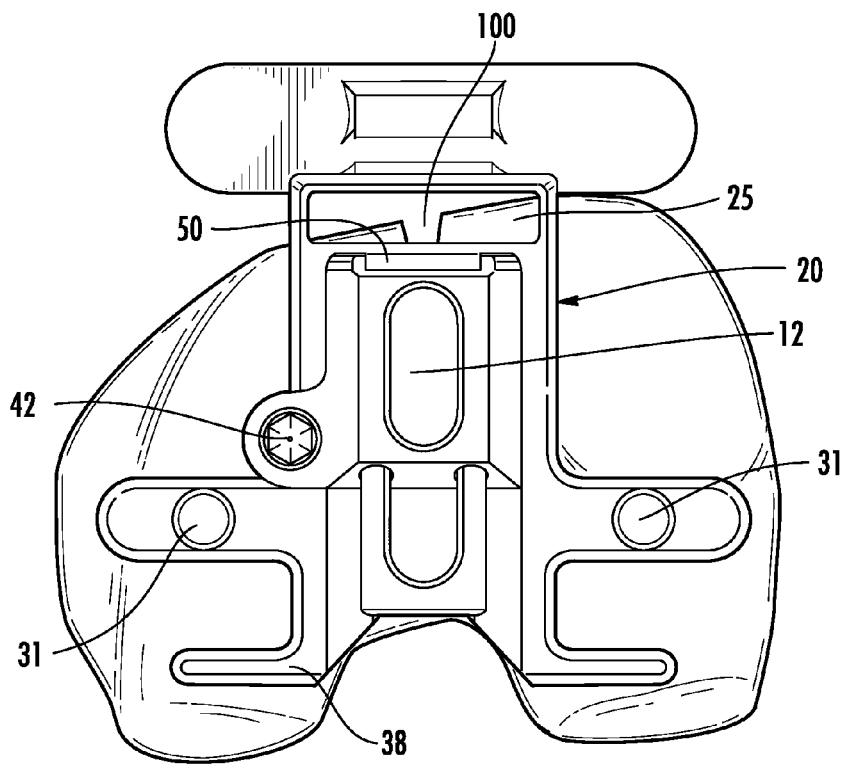
FIG. 5 shows a distal view of one preferred embodiment of a distal cut guide mounted on an intramedullary rod according to the invention.

The valgus rod 12 sets the valgus angled (typically 5°), as well as the external rotation of the resection guide 20. Before inserting the IM rod 10 into the femoral canal, the distal resection guide 20 is preferably loaded onto the valgus rod 12 portion of the IM rod 10, and is locked into position by pushing down the locking shim or IM rod engagement member 50. The IM rod 10 with the attached resection guide 20 is then inserted into the femoral canal. During insertion of the rod 10, the surgeon irrigates and aspirates several times to reduce the chance of a fat embolus, in a manner well known to those of skill in the art. The resection guide 20 should be aligned with the trochlear groove (A/P axis or Whiteside's line), as indicated in FIG. 5. The epicondyles and posterior condyles can be used as a secondary check for femoral rotation. The rod 10 is secured in the femoral canal by impacting until the expanded fluted portion of the rod is flush with the surface of the distal femur.

Once the IM rod 10 is set in position, the surgeon unlocks the distal resection guide 20 and repositions the distal resection guide 20 gently against the distal femur. When the distal resection guide 20 is properly positioned against the distal femur, the surgeon reengages the IM rod engagement member 50 in order to lock the guide 20 in position on the valgus rod 12. The resection guide 20 locking/set screw 42 is loosened to allow the guide 20 to be adjusted anterior/posterior (A/P). The surgeon sets the A/P position of the 4-in-1 resection guide peg holes by initially aligning the anterior window or stylus slot 25 of the guide 20 with the anterior cortex of the distal femur. Alignment with the anterior cortex is preferably achieved by looking through the stylus slot 25 at the rongeur notch 100 that was previously made on the anterior trochlear groove, as indicated in FIG. 5. Although the instruments are designed for use without a stylus, a smooth Steinmann pin (4.88 mm) may be optionally inserted through the window 25 into a notch 100 to act as a stylus. Posteriorly, approximately 10 mm and 8 mm of posterior condyle should be visible below the medial and lateral posterior feet or arms 38, respectively.

Figure 6:
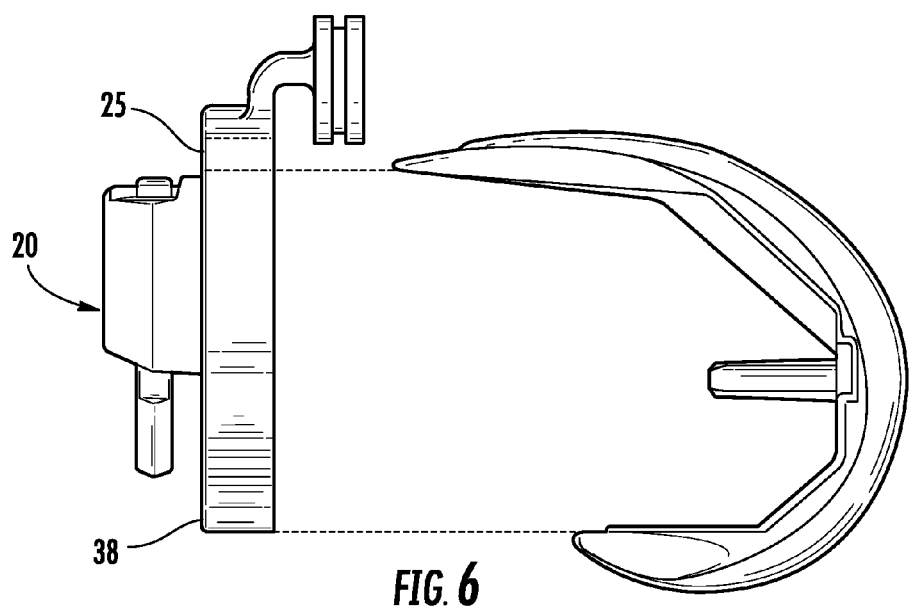
FIG. 6 shows features of the distal cut guide that assist in visualizing the position of box cuts for a correspondingly size femoral knee implant.

As shown in FIG. 6, in a preferred embodiment, the surface of the bottom edge of the anterior window/stylus slot 25 and the bottom surface of the posterior feet 38 represent the internal geometry of the correspondingly sized femoral component. This feature allows the surgeon to readily visualize the location of the anterior and posterior resections. If the surgeon determines that too much or too little posterior condyle will be resected, the A/P position of the cutting guide 20 can be adjusted or the resection guide 20 can be removed and replaced with a different size resection guide 20. To further assist in confirming sizing, the medial/lateral width of the guide 20 is preferably the same width as that of the corresponding size femoral component, as indicated in FIG. 5. Once correct A/P position and size are established, the locking screw 42 is tightened to set the A/P position of the guide 20, and particularly the location of the drill apertures 31, since the apertures 31 will establish the location of the femoral resection block 70. The rod 10 is then impacted into the femur until the femoral pins 39 are fully seated in the most prominent distal condyle. The surgeon then drills through both of the drill apertures 31 to create holes for the femoral resection block 70. The distal resection is carried out using the distal resection slot 27. The most prominent distal condyle provides stability and therefore should be resected last. The guide 20 is unlocked and removed from the valgus rod 12.

Figure 7:
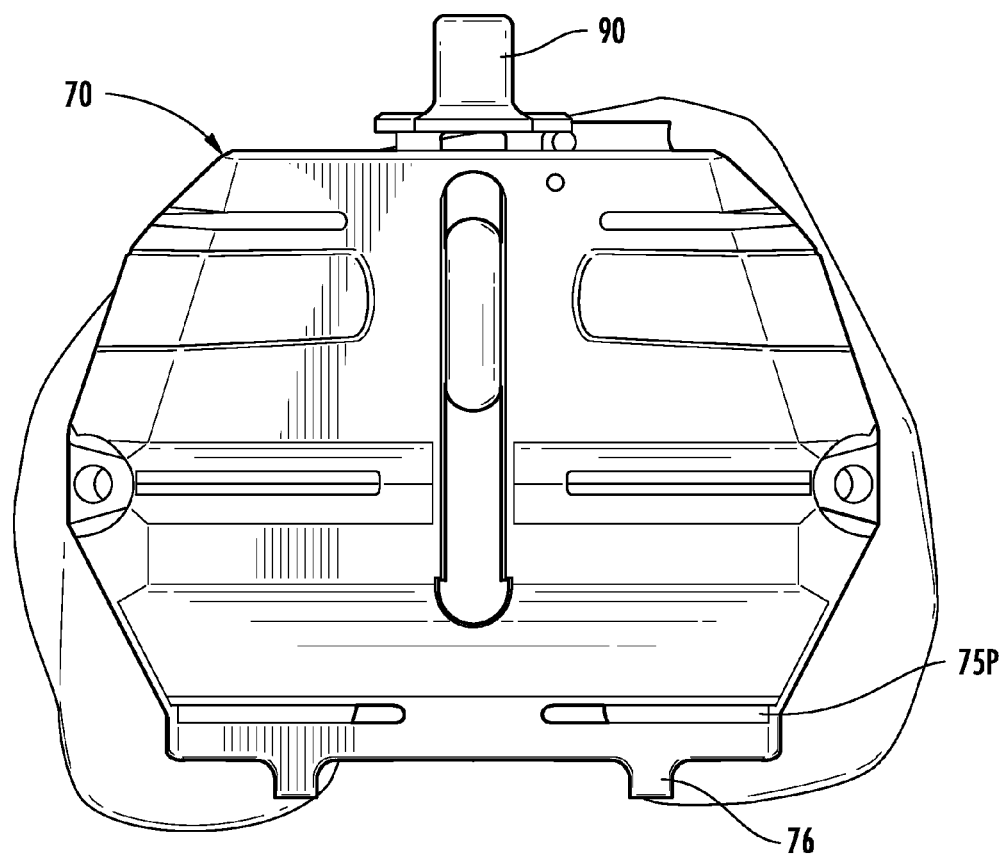
FIG. 7 shows a distal view of one preferred embodiment of a resection block mounted on an intramedullary rod according to the invention.

The surgeon selects a femoral resection block 70 that corresponds in size to the distal resection guide 20. The resection block 70 is slid down the valgus rod 12 until the resection block 70 pegs 73 sink into the peg holes and the block 70 contacts the resected distal femur. Once the resection block 70 is in place, the resection block 70 is locked to the rod by pressing down on the road engagement member 90. If further distal contact is desired, the rod 10 can be impacted more deeply into the femur. Although the instruments are design for pinless TKA procedures, pins can optionally be driven into the pin holes 79 of the block 70 if added stability is desired. To assist with confirming A/P position and sizing, the distance between the posterior resection slot 75P and the posterior edge of the positioning member 76 of the block 70 matches the thickness of the posterior condyle of the corresponding femoral component, as indicated in FIG. 7.

The rod 10 is left in the femur during the box and chamfer resections. Once resections are complete, the rod 10 is removed from the patient. The surgical technique concludes with trochlear groove resection, tibial resection and patellar procedures, in a manner known to those of skill in the art. The tibial resection can be made prior to the femoral resection, at the discretion of the surgeon.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An instrument assembly for use in preparing a distal femur for receipt of an implant, said instrument assembly comprising:

an intramedullary (IM) rod having an intramedullary portion and a valgus portion, said valgus portion including first and second substantially flat surfaces formed on opposing sides, said first and second substantially flat surfaces having a series of engagement members disposed thereon to provide a plurality of engagement positions, each said engagement position for use in fixing resection guides on said valgus portion at said engagement position, a first resection guide instrument having a body defining at least one drill aperture extending through the body and a pair of spaced apart rail members; and an IM rod mount slidingly engaged with the spaced apart rail members of the first resection guide, the IM rod mount defining an aperture that communicates with a slot defined by the spaced apart rail members of the first resection guide, said IM rod mount defining a channel sized and configured to slidably receive an IM engagement member configured to selectively engage and selectively lock on said valgus portion of said IM rod at said engagement positions via said engagement members when the valgus portion of the IM rod mount is received within the slot defined by the spaced apart rail members and within the aperture of the IM rod mount.

2. An instrument assembly of claim 1, wherein said engagement members of said valgus portion of the IM rod include pairs of substantially vertical indents arranged in parallel along the first and second flat surfaces disposed on opposing sides of said valgus portion, and said IM rod engagement member comprising a pair of opposing rail members defining an aperture therebetween, each said rail member having a detent on an internal side thereof, said detents sized and configured to selectively slide into and engage said pairs of indents to thereby lock said first resection guide instrument in a selected engagement position.

3. An instrument assembly of claim 2, wherein the channel of the IM rod mount defines a track on which said rail members of the IM rod engagement member are arranged to slide along.

4. An instrument assembly of claim 2, wherein said first resection guide instrument includes a distal cut guide coupled to the body by a distal resection guide support member that extends from the body, the distal cut guide defining a distal resection slot that extends in a direction that is substantially perpendicular to an axis defined by the at least one drill aperture.

5. An instrument assembly of claim 4, further comprising a second resection guide instrument for making resections corresponding to an internal box geometry of a femoral implant.

6. An instrument assembly of claim 5, wherein the body of the first resection guide instrument defines a pair of drill apertures therethrough, said drill apertures positioned to coincide with femoral pegs extending from a surface of said second resection guide instrument for use in establishing a position for said second resection guide on the femur, the second resection guide defining an aperture for receiving the valgus portion of the IM rod.

7. An instrument assembly of claim 2, further comprising a retaining means for retaining said IM rod engagement member in said first resection guide instrument.

8. An instrument assembly of claim 4, wherein said first resection guide instrument is configured for anterior-posterior adjustment provided by the IM rod mount slidingly engaged to the body of said first resection guide instrument, said aperture of the IM rod mount sized and configured to closely receive said valgus portion of the IM rod so as to substantially prevent rotation of said IM rod mount relative to said IM rod.

9. An instrument assembly of claim 8, further comprising a selective locking mechanism positioned for use in selectively locking said IM rod mount on said first resection guide instrument such that said body and IM rod cannot translate relative to one another.

10. An instrument assembly of claim 6, wherein said first resection guide instrument is configured for anterior-posterior adjustment of said first resection guide relative to said IM rod.

11. An instrument assembly of claim 10, wherein said anterior-posterior adjustment is provided by the IM rod mount's sliding engagement with the body of said first resection guide instrument, said IM rod mount having an aperture sized and configured to closely receive said valgus portion of the IM rod so as to substantially prevent rotation of said IM rod mount relative to said IM rod.

12. An instrument assembly for use in preparing a distal femur for receipt of an implant, said instrument assembly, comprising:

an intramedullary (IM) rod having an intramedullary portion and a valgus portion, said valgus portion having a series of engagement members thereon positioned to provide a plurality of engagement positions, each said engagement position for use in selectively fixing resection instruments on said valgus portion at said engagement position, and a first resection guide instrument including:
a body including first and second rail members defining a slot for receiving the valgus portion of the IM rod therebetween,
an IM rod mount configured to slide along the first and second rail members, the IM rod mount defining first and second apertures, the first aperture sized and configured to receive the valgus portion of the IM rod therein, and
a first IM engagement member configured to be slidably received in the second aperture defined by the IM rod mount, the first IM engagement member having third and fourth rail members each including a respective detent, each of the detents of the third and fourth rail members configured to engage the engagement members disposed on the valgus portion of the IM rod to selectively lock said first resection guide instrument on said valgus portion of the IM rod at said engagement positions when the valgus portion of the IM rod mount is received within the slot defined by the first and second rail members and within the first aperture.

13. The instrument assembly of claim 12, wherein the body of the first resection guide instrument includes a pair of drill guides that extend through the body for guiding a drill.

14. The instrument assembly of claim 13, further comprising:

a second resection guide instrument defining a fourth aperture configured to receive the valgus portion of the IM rod, the second resection guide including a pair of pegs extending from a surface, the pair of pegs disposed on the second resection guide in a position such that they coincide with the pair of drill guides defined by the first resection guide instrument.

15. The instrument assembly of claim 14, wherein the second resection guide instrument defines an engagement track configured to slidably receive a second IM engagement member, the second IM engagement member including:
an anterior cross bar, and
fifth and sixth rail members extending from the anterior cross bar such that they define a slot for receiving the valgus portion of the IM rod, each of the fifth and sixth rail members including an IM rod detent configured to engage the engagement members disposed on the valgus portion of the IM rod to selectively lock the second resection guide on the valgus portion of the IM rod at least one of the engagement positions.

16. The instrument assembly of claim 14, wherein the second resection guide instrument defines at least one anterior resection slot spaced apart and separate from at least one posterior resection slot.

* * * * *

UNITED STATES PATENT AND TRADEMARK OFFICE
CERTIFICATE OF CORRECTION

| | | |
|---|---|---|
| PATENT NO. | : 8,702,714 B2 | Page 1 of 1 |
| APPLICATION NO. | : 11/684395 | |
| DATED | : April 22, 2014 | |
| INVENTOR(S) | : Jeffrey W. Martin et al. | |

It is certified that error appears in the above-identified patent and that said Letters Patent is hereby corrected as shown below:

Title Page:

Item (73) Assignee: Please delete "Microsoft Orthopedics Holdings Inc." and insert -- Microport Orthopedics Holdings Inc. --

Signed and Sealed this
Twenty-first Day of October, 2014

Michelle K. Lee
*Deputy Director of the United States Patent and Trademark Office*